US011426418B2

(12) United States Patent
Shen et al.

(10) Patent No.: US 11,426,418 B2
(45) Date of Patent: Aug. 30, 2022

(54) INJECTABLE LONG-ACTING SEMI-SOLID GEL FORMULATIONS

(71) Applicant: Mira Pharma Corporation, Kenmore, WA (US)

(72) Inventors: Hui Rong Shen, Bothell, WA (US); Na Gan, Bothell, WA (US)

(73) Assignee: MIRA PHARMA CORPORATION, Kenmore, WA (US)

( * ) Notice: Subject to any disclaimer, the term of this patent is extended or adjusted under 35 U.S.C. 154(b) by 0 days.

(21) Appl. No.: 16/792,799

(22) Filed: Feb. 17, 2020

(65) Prior Publication Data

US 2020/0179406 A1 Jun. 11, 2020

(51) Int. Cl.
| | | |
|---|---|---|
| *A61K 31/56* | (2006.01) | |
| *A61K 31/41* | (2006.01) | |
| *A61K 31/215* | (2006.01) | |
| *A61K 31/573* | (2006.01) | |
| *A61K 47/44* | (2017.01) | |
| *A61K 9/00* | (2006.01) | |
| *A61K 31/231* | (2006.01) | |
| *A61K 31/415* | (2006.01) | |
| *A61K 45/06* | (2006.01) | |

(52) U.S. Cl.
CPC .......... *A61K 31/573* (2013.01); *A61K 9/0024* (2013.01); *A61K 31/231* (2013.01); *A61K 31/415* (2013.01); *A61K 31/56* (2013.01); *A61K 45/06* (2013.01); *A61K 47/44* (2013.01)

(58) Field of Classification Search
CPC ..... A61K 31/56; A61K 31/415; A61K 31/215
USPC ........................................ 514/178, 406, 530
See application file for complete search history.

(56) References Cited

U.S. PATENT DOCUMENTS

| | | | |
|---|---|---|---|
| 4,079,038 | A | 3/1978 | Choi et al. |
| 4,093,709 | A | 6/1978 | Choi et al. |
| 4,131,648 | A | 12/1978 | Choi et al. |
| 4,138,344 | A | 2/1979 | Choi et al. |
| 4,180,646 | A | 12/1979 | Choi et al. |
| 4,304,767 | A | 12/1981 | Heller et al. |
| 4,946,931 | A | 8/1990 | Heller et al. |
| 5,700,485 | A | 12/1997 | Berde et al. |
| 6,214,387 | B1 | 4/2001 | Berde et al. |
| 6,521,259 | B1 | 2/2003 | Chasin et al. |
| 6,613,355 | B2 | 9/2003 | Ng et al. |
| 6,790,458 | B2 | 9/2004 | Ng et al. |
| 6,861,068 | B2 | 3/2005 | Ng et al. |
| 6,921,541 | B2 | 7/2005 | Chasin et al. |
| 7,053,209 | B1 | 5/2006 | Gibson et al. |
| 7,666,914 | B2 | 2/2010 | Richlin et al. |
| 8,182,835 | B2 | 5/2012 | Kim et al. |
| 8,221,778 | B2 | 7/2012 | Siegel et al. |
| 9,271,950 | B2 | 3/2016 | Bannister et al. |
| 10,220,093 | B2 | 3/2019 | Shen et al. |
| 10,561,606 | B2 * | 2/2020 | Shen .................. A61K 31/5575 |
| 2004/0001889 | A1 | 1/2004 | Chen et al. |
| 2005/0042194 | A1 | 2/2005 | Ng et al. |
| 2007/0184089 | A1 | 8/2007 | Howie et al. |
| 2014/0155485 | A1 | 6/2014 | Bannister et al. |
| 2015/0297729 | A1 | 10/2015 | Ottoboni et al. |
| 2015/0366967 | A1 | 12/2015 | Shen et al. |

FOREIGN PATENT DOCUMENTS

| | | |
|---|---|---|
| CN | 102458388 A | 5/2012 |
| CN | 102858374 A | 1/2013 |
| CN | 102869344 A | 1/2013 |
| CN | 102892408 A | 1/2013 |
| DE | 10033059 A1 | 1/2002 |
| JP | S62-045538 A | 9/1987 |
| JP | H07-508708 A | 9/1995 |
| JP | H08-143449 A | 6/1996 |
| JP | 2001-261558 A | 9/2001 |
| JP | 2004-501185 A | 1/2004 |
| JP | 2004-506697 A | 3/2004 |
| JP | 2007-521225 A | 8/2007 |
| JP | 2009-518374 A | 5/2009 |
| JP | 2010-522738 A | 7/2010 |
| KR | 10-2012-0046155 A | 5/2012 |
| WO | WO 1993/019736 A1 | 10/1993 |
| WO | WO 1997/044021 A1 | 11/1997 |
| WO | WO 2002/000203 A1 | 1/2002 |
| WO | WO 2002/015937 A2 | 2/2002 |
| WO | WO 2007/066148 A1 | 6/2007 |
| WO | WO 2008/117268 A2 | 10/2008 |
| WO | WO 2010/142457 A1 | 12/2010 |
| WO | WO 2011/075623 A1 | 6/2011 |
| WO | WO 2011/121034 A2 | 10/2011 |

(Continued)

OTHER PUBLICATIONS

G Fetih, "Meloxicam formulations for transdermal delivery: hydrogels versus organogels", 2010, J. Drug Delivery Sci. Technol., 20(6), pp. 451-456.

Fernandez et al., "In Vitro Digestion of the Self-Emulsifying Lipid Excipient Labrasol.RTM. by Gastrointestinal Lipases and Influence of its Colloidal Structure on Lipolysis Rate", 2013, Pharmaceutical Research, vol. 30, Issue 12, pp. 3077-3087.

Yolles et al.; "Sustained Delivery of Drugs From Polymer/Drug Mixtures"; Polymer News; vol. 1; 1970; p. 9-15.

Packhaeuser et al.; "In situ forming parental drug delivery systems: an overview"; European Journal of Pharmaceutics and Biopharmaceutics; vol. 58 No. 2; 2004; p. 445-455.

(Continued)

*Primary Examiner* — Raymond J Henley, III

(74) *Attorney, Agent, or Firm* — Hamre, Schumann, Mueller & Larson, P.C.

(57) ABSTRACT

What is disclosed is a controlled release pharmaceutical composition comprising a biocompatible and bioerodible semi-solid gel comprising a mixture of a triglyceride of ricinoleic acid and a gelling agent, in a formulation with loteprednol, latanoprost, celecoxib, triamcinolone, or betamethasone and, optionally, a second corticosteroid, analgesic, or anti-inflammatory agent.

20 Claims, 5 Drawing Sheets

(56) References Cited

FOREIGN PATENT DOCUMENTS

| WO | WO 2011/121082 A1 | 10/2011 |
|---|---|---|
| WO | WO 2014/134586 A2 | 9/2014 |

OTHER PUBLICATIONS

International Patent Application No. PCT/US2015/050243; Int'l Search Report and the Written Opinion; dated Nov. 23, 2015; 13 pages.

International Patent Application No. PCT/US2015/050243; Int'l Preliminary Report on Patentability; dated Dec. 13, 2016; 21 pages.

Barr et al.; "Post Surgical Pain Management with Poly(ortho esters)"; Advanced Drug Delivery Reviews; Oct. 2002; vol. 54 Issue 7; p. 1041-1048.

Soderberg et al.; "In-vitro release of bupivacaine from injectable lipid formulations investigated by a single drop technique—relation to duration of action in-vivo"; Journal of Pharmacy and Pharmacology; vol. 54 No. 6; 2002; p. 747-755.

Griffin; J. So Cosmetic Chem.; 5:249-35; 1954.

Sokolsky-Papkov et al.; "Poly(DL:Lactic Acid-Castor Oil) 3:7-Bupivacaine Formulation: Reducing Burst Effect Prolongs Efficacy In Vivo"; Journal of Pharmaceutical Sciences; vol. 99 No. 6; Jun. 2010; p. 2732-2738.

Santamaria et al.; "Drug-Delivery systems for prolonged duration local anesthesia"; Materials Today; vol. 20 No. 1; Jan./Feb. 2017; p. 22-31.

Cremer Care; "Softigen 701"; http://www.petercremerna.com/products/657474081; accessed Sep. 26, 2017.

Sokolsky-Papkov et al.; "Prolonged Local Anesthetic Action Through Slow Release from Poly (Lactic Acid Castor Oil)"; 2009; Pharmaceutical Research; 26(1):32-39.

Larsen et al.; "Characteristics of drug substances in oily solutions. Drug release rate, partitioning and solubility"; 2002; International Journal of Pharmaceutics; 232: 107-117.

Zausig et al.; "Lipophilicity of local anesthetics and success of lip emulsion therapy"; 2012; Crit. Care Med; 40(1): 359-360.

Larsen et al.; "Assessment of Drug Release from Oil Depot Formulations Using an in Vitro Model-Potential Applicability in Accelerated Release Testing"; 2008; Drug Development and Industrial Pharmacy; 34:297-304.

Cognis, Nutrition & Health: Product Datasheet: Myrito® 318 PH; https://e-applications.basf-aq.de/data/basf-pcan/pds2/pds2-web.nsf/8C45C964E30F90BDC12573B100597C06/$File/MYRTOL_r_318_PH_E.pdf; accessed Oct. 16, 2016.

Juarez-Soberanez et al.; "GELUCIRE 39/01 as Excipient for Gastroretentive Metronidazole Sustained Delivery"; 2011; International Journal of Pharmacy and Pharmaceutical Sciences; vol. 3 (Supp 2): 86-91.

Graton et al.; "Hydrogen-Bond Accepting Properties of New Heteroaromatic Ring Chemical Motifs: A Theoretical Study"; Journal of Chemical Information and Modeling; vol. 56; 2016; p. 322-334.

Sokolsky-Papkov et al.; "Long-Acting Poly(DL:Lactic Acid-Castor Oil) 3:7-Bupivacaine Formulation: Effect of Hydrophobic Additives"; Pharm. Res.; vol. 28, 2011; p. 3265-3273.

Leslie Harris O'Hanlon; FDA declines approval of testosterone drug for third time; https://www.thelancet.com/journals/landia/article/PIIS2213-8587(13)70040-8/fulltext; The Lancet Diabetes & Endocrinology; vol. 1 Special Issue S14; Jun. 13, 2013; accessed Jan. 17, 2019; 6 pages.

Soderberg et al.; "The "inverted cup"—A novel in vitro release technique for drugs in lipid formulations"; Journal of Controlled Release; vol. 113; 2006; p. 80-88.

Larsen et al.; "In vivo release of bupivacaine from subcutaneously administered oily solution. Comparison with in vitro release"; Journal of Controlled Release; vol. 81; May 2002; p. 145-154.

International Patent Application No. PCT/US2018/064325; Int'l Search Report and the Written Opinion; dated Mar. 28, 2019; 17 pages.

Castillo et al.; "Glucocorticoids prolong rat sciatic nerve blockade in vivo from bupivacaine microspheres"; Anesthesiology; vol. 85; Oct. 1996; p. 1157-1166 (abstract only).

* cited by examiner

INJECTABLE LONG-ACTING SEMI-SOLID GEL FORMULATIONS

CROSS-REFERENCE TO RELATED APPLICATIONS

Applicants hereby incorporate by reference the disclosure of U.S. application Ser. No. 16/212,206, issued U.S. Pat. No. 10,561,606, filed Dec. 6, 2018, and which claims priority to U.S. application Ser. No. 15/833,899, issued U.S. Pat. No. 10,220,093, filed Dec. 6, 2017, hereby incorporated by reference in their entirety.

TECHNICAL FIELD

What is described herein relates to a controlled release pharmaceutical composition comprising loteprednol, latanoprost, celecoxib, triamcinolone, or betamethasone in semi-solid gel comprising a ricinoleic triglyceride and a gelling agent.

BACKGROUND

Controlled release formulation for local delivery of a drug can especially treat inflammation and pain caused by tissue damage caused by disease or injury. The drug delivery vehicle typically consists of a polymeric matrix from which drug is released by diffusion and/or degradation of the matrix. The active ingredient is typically entrapped or encapsulated in microspheres or microparticles which can be administered by injection or infusion in the form of a depot.

Hydrophobic, hydrolysis-resistant polyester-poly(lactic acid-co-castor oil) has been developed for sustained release formulations of bupivacaine. A single injection of a formulation of bupivacaine provides motor blockade for 64 hours and sensory blockade for 96 hours. Sokolsky-Papkov, 2009; *Pharma Res*, 3:7-10, and Sokolsky-Papkov; 2010, *J Pharma Sci*, 99: 2732-38. A significant burst release that led to systemic toxicity for a formulation of 10% bupivacaine, while formulations with 15% bupivacaine showed less burst release.

Larsen, 2008; *Drug Develop Indust Pharm*, 34:297-304 discloses results of measuring rates of release of local anesthetics from various oils using an in vitro measurement dialysis cell to model drug release following intra-articular injection to a joint cavity. Larsen discloses 80% release of bupivacaine from MYRITOL® 318 PH, a fractionated coconut oil consisting of a mixture of $C_8$ and $C_{10}$ saturated fatty acids, in less than two hours.

Castor oil has been used as a solvent in a commercial drug product AVEED® (testosterone undecanoate) injection for testosterone replacement therapy for intramuscular (gluteal muscle) administration. O'Hanlon, 2013, *Lancet*, 1(S14). The United States Food and Drug Administration found inadvertent escape of AVEED® into the vascular system may lead to vascular occlusion and pulmonary oil microembolism. Id. Mechanical occlusion of the pulmonary vasculature from oil microembolization can cause acute transient pulmonary hypertension, resulting in a wide range of symptoms, from mild cough to circulatory collapse.

While these controlled release formulations are useful, their manufacture processes are complicated, cumbersome and expensive. In addition, these formulations are often associated with an initial burst of drug immediately after injection followed by inconsistent and poor drug release kinetics. There remains a need for a more effective sustained released medium to effectively deliver drug locally and produce a prolonged drug release for one week or greater.

SUMMARY

One aspect of the description is a pharmaceutical formulation, comprising
(A) a glyceride mixture comprising
  (i) a triglyceride of ricinoleic acid; and
  (ii) a gelling agent selected from (a) a mixture of $C_{12}$ to $C_{18}$ triglycerides (SUP DM or SUP CM); (b) a mixture of $C_8$ to $C_{18}$ triglycerides (G43/01); (c) a mixture of hydrogenated coco-glycerides (WIT E85 or WIT E76); and (d) a mixture of $C_{10}$ to $C_{18}$ triglycerides (SUP D); or other solid glycerides with a melting point between 37° C. and 75° C.;
wherein the ratio of the triglyceride of ricinoleic acid to the gelling agent is 50:1 to 2:1 (w:w); and
(B) a therapeutically effective amount of an active ingredient selected from the group consisting of loteprednol, latanoprost, celecoxib, triamcinolone, and betamethasone, or a pharmaceutically acceptable salt thereof, and optionally, a second corticosteroid, analgesic or anti-inflammatory compound; wherein total concentration of the active ingredient is 0.01-60 wt % in the glyceride mixture;
wherein the pharmaceutical composition is a semi-solid gel which is biocompatible, bioerodible, and homogeneous, wherein the semi-solid gel has a viscosity of 50-700 cPs at 30° C. Preferably, less than 80% of the active ingredient is released from a depot of the semi-solid gel in less than one week when measured in vitro at 37° C.

In one embodiment of the pharmaceutical formulation, the active ingredient comprises the second corticosteroid, analgesic or anti-inflammatory agent, preferably wherein the corticosteroid is a glucocorticosteroid; or wherein the anti-inflammatory agent is a non-steroidal anti-inflammatory agent (NSAID) selected from the group consisting of ketoprofen, naproxen, meloxicam, COX-1 inhibitors, and COX-2 inhibitors.

In another embodiment, the glyceride mixture comprises a ratio of the triglyceride of ricinoleic acid to the gelling agent having a relative concentration of 50:1 to 2:1, preferably 8:1 to 2.5:1, most preferably 6:1 to 3:1 (w:w).

In another embodiment, 80% of the active ingredient is released from a depot of the semi-solid gel in 1 to 16 weeks when measured in vitro at 37° C.

In another embodiment, the viscosity is 200 to 400 cPs at 30° C.

In another embodiment, the pharmaceutical composition releases the active ingredient for more than one week when measured in vitro at 37° C.

In another embodiment, the pharmaceutical composition releases the active ingredient for more than four weeks when measured in vitro at 37° C.

In another embodiment, the glyceride mixture has an aqueous solubility of less than 1 mg/ml or less than 0.1 mg/ml in a buffer of physiological pH at 37° C.

In another aspect of the description, the triglyceride of ricinoleic acid consists of castor oil and the gelling agent comprises SUP DM or SUP-CM, the ratio of castor oil:SUP DM/CM is preferably 6:1 to 3:1 (w:w), and has an aqueous solubility of less than 1 mg/ml or less than 0.1 mg/ml in a buffer of physiological pH at 37° C. Preferably the pharmaceutical composition comprising this mixture releases active ingredient for at least one to two weeks when measured in vitro at 37° C.

DETAILED DESCRIPTION

Advantages of Bioerodible Semi-Solid Gel Technology

Figure 1:
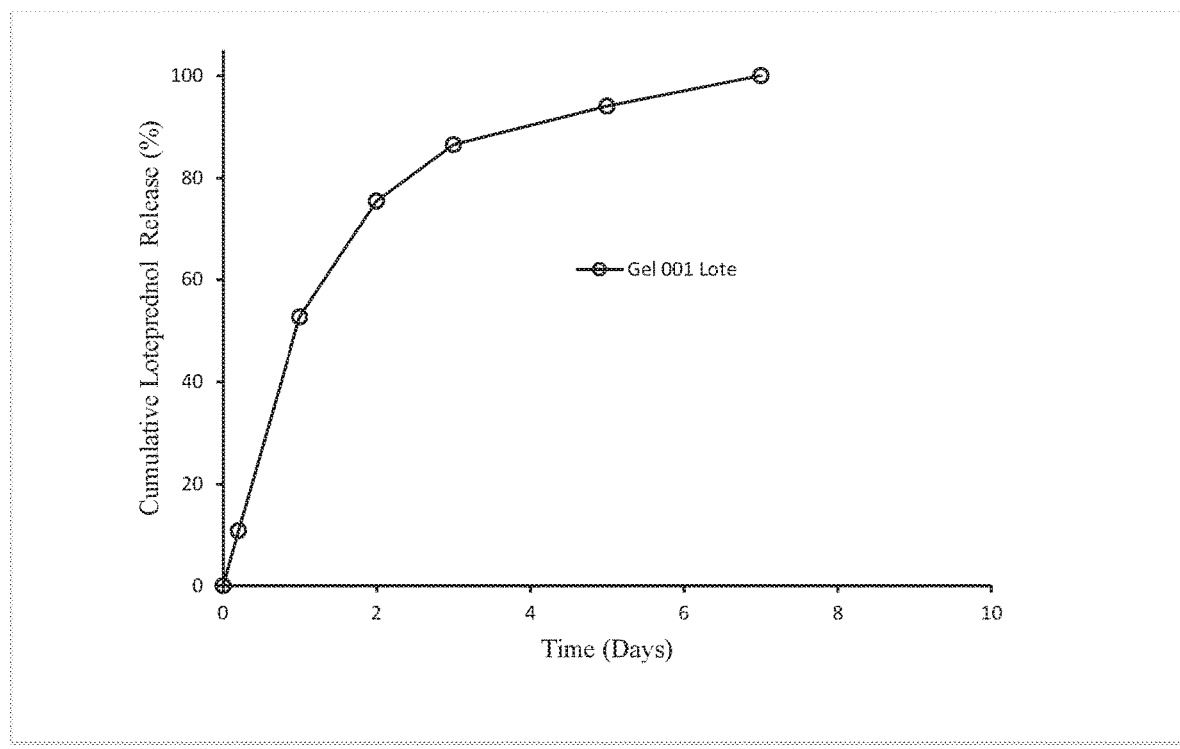
FIG. 1 shows release of loteprednol (LOTE) from a formulation comprising castor oil gel gelled by SUP DM. Gel 001 LOTE: CO/SUP DM/LOTE (77.8/19.5/2.7) in phosphate-buffered saline (PBS), pH 7.4, 37° C.

The formulations described herein provide a prolonged period of local release such that therapeutic concentrations of a drug are achieved rapidly and maintained for at least one week. The benefit of the prolonged release profile is to maintain higher levels of active drug at the site of the disease or injury over time and thereby to provide a greater therapeutic effect for at least one week.

Benefits of Bioerodible, Semi-Solid Gel Technology:

The bioerodible, semi-solid gel formulations described herein provide the advantage of providing sustained release of a drug without a significant initial burst. In vitro drug release and animal studies have shown that injectables based on our bioerodible semi-solid gel technology produce less post-injection burst that is found with other injectable controlled release technologies.

Concentration of active ingredient in the semi-solid gel technology described herein are preferably at a concentration of 1-20 wt %, which is considerably greater than what is typical with other controlled release technologies.

The semi-solid gel formulations exhibit described herein have low viscosity, and are therefore injectable through a 21 G to 25 G needle. Additionally, since the semi-solid gel formulations described herein have a higher capacity for drug loading, less volume of drug product is required to be injected. Small injection volumes and low viscosity semi-solid formulations result in easier and less painful administration. Polyorthoester semi-solid formulations have a viscosity of thousands of mPa·s, and are difficult to inject with a 21 G needle.

The formulations described herein comprise glycerides with natural fatty acids. These compounds are readily hydrolyzed to glycerol and free fatty acids by lipase. These compounds are non-toxic and exhibit excellent biocompatibility in the body. The formulations described herein are biodegradable, bioerodible, and fully resorbable. In animal studies, at two weeks after dosing, no adverse effect of the semi-solid formulation on wound healing was observed. The administration site appeared to be pinkish, and the sciatic nerve appeared to be normal, no inflammation, necrosis, ulceration, or infection was observed.

Compared to microspheres and other polymer-based controlled release injectable systems, the semi-solid gel formulations described herein are readily manufactured at low cost. The active ingredient(s) and semi-solid gel vehicle components are simply mixed at without the use of solvents at relatively low elevated temperatures. Note that since relatively low-melting point solid glycerides (less than 50° C.) (gelling agents) are used, the manufacturing process is at about 60° C.

Further, the formulations described herein can be administered directly for site-specific delivery. Since the formulations provide a sustained drug release over a period of several weeks resulting in increased duration of pharmacological action, and reduced frequency of drug administration. The formulations also produce reduced side effects (due to local drug delivery) when compared with systemic administration. The ease of use should produce improved patient compliance.

Definitions

All technical and scientific terms are used herein according to their conventional definitions as they are commonly used and understood by those of ordinary skill in the art of drug delivery. Specific terms for the description herein will be defined below.

"Active agent" as used herein consists of loteprednol (ethyl 4-(8-chloro-5,6-dihydro-11-benzo 5,6 cyclohept a 1,2-bpy ridin-11-ylid ene)-1-piperidinecarboxylate), latanoprost (isopropyl-(Z)-7 (1R,2R,3R,5S) 3.5-dihydroxy-2-(3R)-3-hydroxy-5-phenylpentyl)cyclopentyl 5-heptanoate)), celecoxib (4-[5-(4-methylphenyl)-3-(trifluoromethyl)pyrazol-1-yl]benzenesulfonamide), triamcinolone ((11β,16α)-9-fluoro-11,16,17,21-tetrahydroxypregna-1,4-diene-3,20-dione), and betamethasone ((8S,9R,10S,11S,13S,14S,16S,17R)-9-fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one), or a pharmaceutically acceptable salt suitable for local treatment thereof, and optionally, a second corticosteroid, analgesic or anti-inflammatory compound.

Abbreviations used: betamethasone, BET; betamethasone valerate, BETV; celecoxib, CEL; ketoprofen, KETO; methylprednisolone, MP; triamcinolone acetonide, TA; meloxicam, MELO; loteprednol etabonate, LOTE; latanoprost, LATA; castor oil, CO.

The term "semi-solid" denotes the physical state of a material that is flowable under a moderate pressure. More specifically, the semi-solid material has a viscosity of 50 to 700 cps (mPa·s) at 30° C.

The term "bioerodible" refers to a material that gradually decomposes, dissolves, hydrolyzes and/or erodes in situ. Generally, the "bioerodible" semi-solid gel described herein are materials that are degraded in situ primarily through lipolysis and hydrolysis.

The semi-solid lipids, solvent and other agents of the description must be "biocompatible"; that is, they must not cause irritation or necrosis in the environment of use. The environment of use is a fluid environment and may comprise a subcutaneous, subconjunctival, intramuscular, intravascular, intramyocardial, adventitial, intratumoral, or intracerebral portion, wound sites, tight joint spaces or body cavity of a human or animal.

Castor Oil and Gelling Agents

Castor oil injectable grade (USP-NF41-36 2S) is a preferred triglyceride component of the semi-solid formulations described herein. Castor oil is a triglyceride in which approximately 90% of fatty acid chains are ricinoleates. Oleate and linoleates are the other significant components.

Castor oil is a liquid with a viscosity of approximately 700 cPs at 25° C. Although it is a relatively viscous vegetable oil, when a drop of castor oil is added to water or PBS at 37° C., it will immediately spread out and dissipate on the surface of aqueous solution and eventually form small droplets. Therefore, castor oil is not suitable to serve as a sustained release depot. Liquid castor oil for injectable dosage forms is sold as "Super Refined Castor Oil" which meet the standard of USP monograph USP-NF41-36 2S, and is supplied by Croda Inc. and Ambuja Solvex Pvt. Ltd.

Hydrogenated castor oil is a hard, high melting point (85 to 88° C.) wax that has been used as an extended release agent in pharmaceutical formulations as a solvent to emulsify and solubilize other water-insoluble substances used most widely in topical formulations, including ophthalmic preparations.

What is disclosed herein is the surprising finding that when a solid gelling agent selected from $C_{12}$ to $C_{18}$ triglycerides (SUP DM or SUP CM),
a mixture of $C_8$ to $C_{18}$ triglycerides (G43/01),
mixtures of hydrogenated coco-glycerides (WIT E85 and WIT E76),
a mixture of $C_{10}$ to $C_{18}$ triglycerides (SUP D), and
or other solid glycerides with a melting point between 37° C. and 75° C.

is added to castor oil, liquid castor oil 700 cPs changes into a soft semi-solid gel. For example, when SUP DM is at 5%, gelation occurs very slowly at room temperature (flowable at 37° C. body temperature). Gelation occurs at room temperature when SUP DM is at or above 10%. As the amount of SUP DM increases, it takes less time to start gelation. At a 20% level, the semi-solid gel formed is still a soft gel and is injectable with 21 G needle. When the amount of SUP DM increases to 30%, the semi-solid gel formed became a relatively hard gel and is difficult to be injected with a 21 G needle.

The castor oil gels formed are characterized by their property of changing from a fluid at room temperature to a gel at room temperature, and retain as a well-defined gel when the semi-solid gel is placed into in water at 37° C.

In addition, that castor oil slowly released into water, probably due to the cohesive interaction between castor oil and the gelling agent and the relatively hydrophobic semi-solid gel structure. Results herein show the release kinetics of active drugs from formulations comprising CO. A stable gel formulation will ensure the formulation remain as a long-lasting well-defined depot once administrated into the human body to control the gradual release of active drugs and could prevent undesirably rapid release of castor oil into animal or human's bloodstream causing vascular occlusion and potential pulmonary oil microembolism. Furthermore, the low viscosity (approximately 350 cPs at 30° C.) of the soft semi-solid gel formulation allows it to be readily injected through a 21 G needle to form a depot for local drug delivery.

The gelling agents for the present description are pharmaceutically acceptable and castor oil-compatible materials. As castor oil is a mixture of triglycerides, the solid or semi-solid glycerides are compatible with castor oil to form a semi-solid gel.

More specifically, suitable gelling agents can be solid triglycerides of mixed esters, solid partial glycerides of fatty acids, mixtures of triglyceride, diglyceride or monoglyceride, and other castor oil compatible gelling agents such as sterol ester lanolin. Since these gelling agents are structurally similar to castor oil, they are expected to be compatible. Physically, these materials can be in the form of solid or semi-solid lipid are at room temperature and should also have low solubility with an aqueous solubility of less than 1 mg/mL in physiological pH buffer at 37° C., preferably less than 0.1 mg/mL. If the gelling agent is too hydrophilic and water soluble, it will cause a significant burst of the active drug(s), especially when the active drugs are relatively soluble, which may cause undesirable side effects. If the gelling agent is significantly more insoluble than the main semi-solid lipid, it will retain in the body significantly longer when the active drug and the main semi-solid lipid is completely dissolved and resorbed by the body.

Useful solid or semi-solid lipid compatible with castor oil to form a semi-solid gel delivery vehicle for active drugs include solid triglycerides of mixed esters, solid partial glycerides of fatty acids, mixtures of triglyceride, diglyceride or monoglyceride, and other castor oil compatible gelling agents such as sterol ester lanolin with a melting point of less than 100° C., preferably between 37° C. and 75° C., and more preferably between 37° C. and 50° C. When the melting point gets too high, especially at higher concentration (>20 wt %), it will cause the hardening of the semisolid gel, and affect the injectability of the semi-solid gel formulations.

Solid triglycerides that can be added to castor oil to form a semi-solid gel include SUP DM, a mixture of $C_{12}$ to $C_{18}$ triglycerides with a melting point of 42.5° C. to 46° C.; SUPPOCIRE® D (SUP D), a mixture of $C_{12}$ to $C_{18}$ triglycerides with a melting point of 42° C. to 45° C.; SUPPOCIRE® CM (SUP CM), a mixture of $C_{12}$ to $C_{18}$ triglycerides with a melting point of 37.8° C. to 39.8° C.; SOFTISAN® 378 (S378), a triglycerides of $C_{10}$ to $C_{18}$ fatty acids with a melting point of 39° C. to 42° C.; and hydrogenated castor oil with a melting point of 85° C. to 88°.

Solid partial glycerides of fatty acids that can be added to castor oil to form a semi-solid gel include GELUCIRE 43/01 (G43/01) glyceride of $C_{12}$ to $C_{18}$ fatty acids with a melting point of 42° C. to 45° C.; GELEOL™, a glyceryl monostearate with a melting point of 54° C. to 64° C.; GELUCIRE 39/01 (G39/01) a glyceride mixture of mono-, di-, and triglycerides of $C_{12}$ to $C_{18}$ fatty acids with a melting point of 37° C. to 40° C.; and COMPRITOL® 888 ATO, glyceryl behenate with a melting point of 65° C. to 77° C.

Mixtures of triglyceride, diglyceride or monoglyceride that can be added to castor oil to form a semi-solid gel include WITEPSOL® E85 (WIT E85) with a melting point of 42° C. to 44° C.; and WITEPSOL® E76 (WIT E76) with a melting point of 37° C. to 39° C.

Furthermore, other castor oil compatible gelling agents such as sterol ester lanolin with a melting point of 38° can be added to castor oil to form a semi-solid gel.

The concentrations of gelling agents added to castor oil may vary. For example, the concentration (wt %) of the gelling agents may be in the range of about 1 to 30 wt %, preferably about 5 to 25 wt %.

The castor oil mixed with the gelling agents (the final delivery vehicle), and the delivery vehicle with the active ingredients can form a defined long-lasting depot once administered into the body at 37° C., and will gradually degrade/erode, and be dissolved into the body liquids, and the semi-solid lipids will eventually be hydrolyzed to natural free glycerol and free fatty acids by lipase through a process called lipolysis.

Preparation of Castor Oil Semi-Solid Gel Formulation

The castor oil semi-solid gel formulation of an active agent described herein may be prepared by directly mixing together with castor oil and the gelling excipient, or by mixing with the semi-solid gel already formed. The mechanical mixing process is performed at a suitable temperature, typically between 60° C. and 90° C., to completely melt the gelling excipients and castor oil into a solution, and dissolve or mill by any mechanical means the active drugs to from a clear solution or a homogeneous suspension. A vacuum may be applied to avoid air bubbles, and nitrogen may be applied to reduce oxidation of active drugs and the delivery vehicle components. After achieving a homogeneous and uniform pharmaceutical composition, the active agent semi-solid gel formulation can be cooled down to room temperature.

Semi-Solid Gel Pharmaceutical Compositions Comprising Active Ingredient

Preferred active ingredient for local delivery are selected from the group consisting of celecoxib, triamcinolone, and betamethasone, loteprednol and latanoprost, or other pharmaceutically acceptable active ingredient.

The active agents (free base) can be readily converted into a salt with fatty acids and other pharmaceutically acceptable acids. Both saturated and unsaturated fatty acids such as lauric acid, myristic acid, palmitic acid, and oleic acid are natural fatty acids, and can be used. This conversion can increase its compatibility and solubility in the semi-solid vehicle. The selected active agents can be converted into a salt in advance before being incorporated into the semi-solid vehicle or can be added into the semi-solid vehicle simultaneously at a 1:1 molar ratio or other molar ratios during the formulation manufacturing process.

The amount of active ingredient present in the composition can vary over a wide range depending on a number of factors, such as the therapeutically effective dose of the active drug, the desired duration of biological or therapeutic effect, and the release profile of the composition. The concentration of the active ingredient may be in the range of about 0.01 to 60 wt %, preferably about 1 to 40 wt %, or more preferably about 1 to 20 wt %.

The glyceride mixture comprises a ratio of the triglyceride of ricinoleic acid to the gelling agent having a relative concentration of 50:1 to 2:1, preferably 8:1 to 2.5:1, most preferably 6:1 to 3:1 (w:w).

The concentration (wt %) of the gelling agents may be in the range of about 1 to 30 wt %, preferably about 5 to 25 wt %.

In addition, other pharmaceutically acceptable agents such as penetration enhancers, including natural penetration ingredients such as oleic acid, linoleic acid, and synthetic ingredients such as azone, propylene glycol, ethoxydiglycol, N-methylpyrrolidone, methylsulfonylmethane, dimethyl sulfoxide, antioxidants, preservatives, and other inert agents such as coloring or flavoring agents may be added.

This pharmaceutical semi-solid gel composition of the present semi-solid formulation described herein has a smooth semi-solid gel texture. Therefore, the composition can be filled into syringes with a 21 G to 25 G needle for subcutaneous, subconjunctival, intradermal, intramuscular, epidural, intraarticular, intravitreal, or intrathecal injection, or can also be conveniently applied onto already-open sites such as surgical wounds/site or exposed skin or mucous membrane.

After administration by injection or topical application, the active agent is released from the composition in a sustained and controlled manner. The rate of release may be regulated in a variety of ways to accommodate the desired duration of therapeutic effect. For example, the rate may be increased or decreased by using different level of gelling agents. It may also be altered by selecting different gelling agents or by changing their amount, or the combination thereof. In addition, lower water solubility forms of active ingredient such as their base forms, or as complexes with fatty acids may be used to delay the release of active ingredient.

Pharmaceutical Uses

The semi-solid gel pharmaceutical compositions of the present description can be filled into syringes and directly injected locally at the site of disease or injury. This drug product enables localized treatment.

Other Semi-Solid Gel Pharmaceutical Formulations

Exemplary compositions of this semi-solid formulation described herein, and their uses, include: compositions containing ophthalmic drugs, corticosteroid such as loteprednol for the treatment of inflammation of the eye; glaucoma drug such as latanoprost for the treatment of open-angle glaucoma or ocular hypertension; antiangiogenic agents such as combrestatin for the treatment of macular degeneration and retinal angiogenesis; and other compositions for the controlled release of ophthalmic drugs to the eye. Despite the widespread use of topical eyedrop preparations, this means of drug delivery is suboptimal and might be associated with poor patient compliance. Largely across preparations, there is poor bioavailability from eyedrops; experts estimate less than 5% of the applied dose of topical preparations reaches the intraocular tissues. Studies show wide variations in patients' ability to successfully administer drops to the ocular surface.

The amount of active ingredient present in the composition can vary over a wide range depending on a number of factors, such as the therapeutically effective dose of the active drug, the desired duration of biological or therapeutic effect, and the release profile of the composition. The concentration of the active agent may be in the range of about 0.01 to 60 wt %, preferably about 1 to 10 wt %. The formulations described herein for injection have another advantage over many topical formulations: the injectable formulation contain no preservatives, e.g., benzalkonium chloride (BAK).

1. Background

Castor Oil (CO)

CO is a consistent material with respect to composition and physical properties such as viscosity. Castor oil is an oil solution, not a sustainable "depot". Upon injection, it can cause vascular occlusion and potential pulmonary oil microembolism, especially using a large bolus (3-5 mL). Rapid release or dumping of relatively large volume of castor oil could become a safety issue.

Gelling Agents

One object of studies summarized herein was to change castor oil into a stable gel that controls the release of a solubilized drug, and also controls the release of castor oil into surrounding tissue. Another object was to prevent rapid release of drug and/or dumping of castor oil.

Pharmaceutically acceptable gelling agents were tested. Aluminum salts of fatty acids such as aluminum stearate and magnesium stearate are commonly used. Polymers such as carboxymethyl cellulose, polyvinyl alcohol, and polyvinylpyrrolidone are also used. Polysaccharides such as natural pectin and starches are typically used for aqueous systems, and are not compatible with CO. It was found that pectin from different sources provides different gelling abilities, due to variations in molecular size and chemical composition. Like other natural polymers, a major problem with pectin is inconsistency in reproducibility between samples, which may result in poor reproducibility in drug delivery characteristics.

Gelling experiments were performed as follows. The targeted amounts of gelling agents and the castor oil was weighed and transferred to a glass vial and sealed. The mixture was heated to about 96° C. in a water bath for about ten minutes, and then vortexed for one minute. The procedure was repeated three times with a total of 30 minutes to dissolve the gelling agents into castor oil. Three polymers, carboxymethyl cellulose, polyvinyl alcohol, and polyvinylpyrrolidone were tested at 0.2% level (2 mg of polymer was added to 1 g of castor oil, and heated and vortexed at 96° C. for 30 minutes. None of them were soluble in castor oil.

Aluminum distearate was tested at 0.1%, 0.5%, and 1% in castor oil. Results showed that the solubility of aluminum distearate in castor oil was less than 0.1% after being heated and vortexed at 96° C. for 30 minutes. No gel formation occurred when cooled to room temperature overnight.

None of the above "gelling agents" tested were soluble and compatible with CO.

Relatively high melting point glycerides were then tested measuring the time from start gelation and complete gelation, and release of castor oil at 37° C. in water. In vitro, and in vivo studies showed that formulations comprising relatively high melting point glycerides and CO provided significantly better controlled local anesthetic release, and thus improved analgesic efficacy. Further, CO is a triglyceride, and exhibited less inflammation than commercial 5701, which is a mixture-of mono-, di- and triglycerides.

2. Semi-Solid Gel Formulation for Local Delivery a. Bupivacaine Solubility in Neat Castor Oil The solubility of bupivacaine in castor oil was determined by dissolving bupivacaine into castor oil by mixing the components at an elevated temperature of 70-80° C. to form a clear solution which resulted as a clear oil solution when cooled down to ambient temperature. Bupivacaine ranging from 5% up to 20% can be readily dissolved into castor oil.

b. Required Amount of SUP DM to Form Castor Oil Gel

The required amount of gelling agent to form a castor oil semi-solid gel formulation in the presence of 8 wt % bupivacaine was determined by mixing the components at an elevated temperature of 70-80° C. form a clear solution while mixing and resulted as a homogeneous semi-transparent or opaque gel formulation after cooling down to room temperature. The results in Table 1 show that gelling agent SUP DM ranging from 10% up to 30% can form a semi-transparent or opaque semi-solid gel formulation.

When the gelling agent SUP DM is at 5%, gelation occurs very slowly at room temperature (flowable at 37° C. body temperature). When SUP DM is at or above 10%, gelation occurs at 21° C. As the amount of SUP DM increase, it takes less time to start gelation. At 20% level, the semi-solid gel formed is still a soft gel and is injectable with 21 G needle. When the amount of SUP DM increases to 30%, the semi-solid gel formed became a relatively hard gel and is difficult to be injected with a 21 G needle. The results suggest that 10% to 20% of SUP DM can be used as a gelling agent to form a nice bupivacaine semi-solid gel formulation with good syringeability.

TABLE 1

: Castor oil/gelling agent ratio study:
bupivacaine semi-solid gel formulations

| Sample ID | Castor Oil (g) | SUP DM (g) | Bup Amount (mg) | Required time to start gelation at 21° C. (minutes) | Required time to complete gelation at 21° C. (minutes) |
|---|---|---|---|---|---|
| Gel F01 | 0.87 | 0.05 | 80 | 20:00 | 43:00 |
| Gel F02 | 0.82 | 0.10 | 80 | 10:00 | 21:00 |
| Gel F03 | 0.80 | 0.12 | 80 | 8:30 | 18:00 |
| Gel F04 | 0.77 | 0.15 | 80 | 7:45 | 13:00 |
| Gel F05 | 0.72 | 0.20 | 80 | 6:15 | 11:00 |
| Gel F06 | 0.62 | 0.30 | 80 | 5:25 | 8:00 |

The castor oil gels formed are characterized by their property of changing from a fluid at room temperature to a gel at room temperature, and retain as a well-defined gel when the semi-solid gel is placed into in water at 37° C. A castor oil bupivacaine semi-solid gel formulation was prepared with 15% SUP DM when placed and tested in water at 37° C.

In addition, it was observed that castor oil was very slowly released out into water, potentially due to the cohesive interaction between castor oil and the gelling agent and the relatively hydrophobic semi-solid gel structure.

Bupivacaine ranging from 5% up to 15% can be readily dissolved into the semi-solid lipid mixture of castor oil and SUP DM mixture. Although up to 15% of bupivacaine was soluble in the final semi-solid gel formulation mixture, less than 10% was selected to avoid potential drug crystallization during long term storage.

c. Additional Gelling Agents

Additional castor oil compatible gelling agents suitable to form a local anesthetic semi-solid gel formulation were identified using the above experimental approach. Besides SUP DM, a mixture of $C_{12}$ to $C_{18}$ triglycerides with a melting point of 42.5° C. to 46° C., other solid or semi-solid triglycerides include SUPPOCIRE® D (SUP D), a mixture of $C_{12}$ to $C_{18}$ triglycerides with a melting point of 42° C. to 45° C.; SUPPOCIRE® CM (SUP CM) a mixture of $C_{12}$ to $C_{18}$ triglycerides with a melting point of 37.8° C. to 39.8° C.; SOFTISAN® 378 (S378), a triglycerides of $C_{10}$ to $C_{18}$ fatty acids with a melting point of 39° C. to 42° C.; and hydrogenated castor oil with a melting point of 85° C. to 88° C. These were also tested as gelling agents to enable castor oil to form semi-solid gel formulations in the presence of active ingredient.

The semi-solid pharmaceutical compositions herein were prepared as follows: The active ingredient, castor oil, and gelling agents were added to a glass container, and then heated to about 60° C. to 90° C. depending on the properties of local anesthetics and the vehicle components used to completely melt semi-solid lipid and gelling agents into a solution, and the active ingredients were incorporated into the delivery vehicle to form a homogeneous gel during mixing. After achieving a homogeneous and uniform pharmaceutical composition, the local anesthetic semi-solid formulation is cooled down to ambient temperature naturally.

EXAMPLES

Commercial products were used according to Table 2, which are available in GMP quality and quantity.

TABLE 2

Commercial triglyceride mixtures

| Castor oil | ricinoleic acid triglycerides |
|---|---|
| SUPPOCIRE ® DM (SUP DM) | a mixture of $C_{12}$ to $C_{18}$ triglycerides with a melting point of 42.5° C. to 46° C. |
| SUPPOCIRE ® D (SUP D) | a mixture of $C_{10}$ to $C_{18}$ triglycerides with a melting point of 42° C. to 45° C. |
| SUPPOCIRE ® CM (SUP CM) | a mixture of $C_{12}$ to $C_{18}$ triglycerides with a melting point of 37.8° C. to39.8° C. |
| SOFTISAN ® 378 (S378) | a mixture of $C_{10}$ to $C_{18}$ triglycerides with a melting point of 39° C. to 42° C. |
| GELUCIRE 43/01 (G43/01) | a mixture of $C_8$ to $C_{18}$ triglycerides with a melting point of 42° C. to 45° C. |
| GELUCIRE 39/01 (G39/01) | a mixture of $C_{12}$ to $C_{18}$ triglycerides with a melting point of 37° C. to 40° C. |
| GELEOL ™ (GEL) | a glyceryl monostearate with a melting point of 54° C. to 64° C. |
| COMPRITOL ® 888 ATO (COM) | glyceryl behenate with a melting point of 65° C. to 77° C. |
| WITEPSOL ® E 85 (WIT E85) | hydrogenated coco-glycerides with a melting point of 42° C. to 44° C. |
| WITEPSOL ® E 76 (WIT E76) | Hydrogenated coco-glycerides with a melting point of 37° C. to 39° C. |
| SOFTIGEN ® 701 (S701) | ricinoleic acid partial glycerides |

Example 1. SUP D

The SUP D mixture of $C_{12}$ to $C_{18}$ triglycerides has a melting point of 42° to 45° C. The CO and SUP D ratio study is shown in Table 3. The targeted amount of each component was weighed to a glass vial and heated to about 75° C. in a water bath, and mixed/vortexed until all components are completely dissolved and form a clear solution.

It takes about the same time for SUP DM and SUP D to start and complete gelation because they exhibit similar properties and melting points. Approximately 1 mL of the hot solution was filled into a 5 mL prefilled syringe, and steam-sterilized under 121° C. for 20 minutes. They appeared as a homogeneous opaque gel with or without steam sterilization after cooling down to room temperature at 10 to 20 wt % gelling agent level, and are injectable with 21 G needle.

TABLE 3

CO and SUP D ratio study

| Sample ID | CO (g) | SUP D (g) | BUP (mg) |
|---|---|---|---|
| SUP D F01 | 1.64 | 0.20 | 160 |
| SUP D F02 | 1.54 | 0.30 | 160 |
| SUP D F03 | 1.44 | 0.40 | 160 |

Example 2. SUP CM

The SUP CM mixture of $C_{12}$ to $C_{18}$ triglycerides has a melting point of 37.8 to 39.8° C. The CO and SUP CM ratio study is shown in Table 4. The targeted amount of each component was weighed to a glass vial and heated to about 75° C. in a water bath, and mixed/vortexed until all components are completely dissolved and form a clear solution.

The SUP CM mixture of $C_{12}$ to $C_{18}$ triglycerides has a melting point of 37.8 to 39.8° C. The CO and SUP CM ratio study is shown in Table 4. The targeted amount of each component was weighed to a glass vial and heated to about 75° C. in a water bath, and mixed/vortexed until all components are completely dissolved and form a clear solution.

It takes longer for SUP CM than those for SUP DM to start and complete gelation because SUP CM has lower melting point.

Approximately 1 mL of the hot solution was filled into a 5 mL prefilled syringe, and steam-sterilized under 121° C. for 20 minutes. They appeared as a homogeneous opaque gel with or without steam sterilization after cooling down to room temperature at 10 to 20 wt % gelling agent level, and are injectable with 21 G needle.

TABLE 4

CO and SUP CM ratio study

| Sample ID | CO (g) | SUP CM (g) | BUP (mg) |
|---|---|---|---|
| SUP CM F01 | 1.64 | 0.20 | 160 |
| SUP CM F02 | 1.54 | 0.30 | 160 |
| SUP CM F03 | 1.44 | 0.40 | 160 |

Example 3. S378

The S378 mixture of triglycerides of $C_{10}$ to $C_{18}$ fatty acids has a melting point of 39° to 42° C. and is in the form of a semi-solid. Its gelling power is less than those in the form of hard solid, higher amount/concentration compared to other solid triglyceride was used. At 40 wt % S378 level, it takes about 6:30 minutes to start gelation, but 36:00 minutes to complete gelation.

The CO and S378 ratio study is shown in Table 5. The targeted amount of each component was weighed to a glass vial and heated to about 75° C. in a water bath, and mixed/vortexed until all components are completely dissolved and form a clear solution.

Approximately 1 mL of the hot solution was filled into a 5 mL prefilled syringe, and steam-sterilized under 121° C. for 20 minutes. They appeared as a homogeneous opaque gel with or without steam sterilization after cooling down to room temperature at 30 to 50 wt % gelling agent level, and are injectable with 21 G needle. At 20% level, the formulation is still flowable after cooling down to room temperature.

TABLE 5

CO and S378 ratio study

| Sample ID | CO (g) | S378 (g) | BUP (mg) |
|---|---|---|---|
| S378 F01 | 1.44 | 0.40 | 160 |
| S378 F02 | 1.24 | 0.60 | 160 |
| S378 F03 | 1.04 | 0.80 | 160 |
| S378 F04 | 0.84 | 1.00 | 160 |

Example 4. HCO

Hydrogenated castor oil solid triglyceride (HCO) has a relatively high melting point of 85 to 88° C. Due to its high melting point, this gelling agent need to be heated above 88°

C. to be completely melted and homogeneously mixed with castor oil to form a semi-solid gel.

The CO and HCO ratio study is shown in Table 6. The targeted amount of each component was weighed to a glass vial and heated to about 90° C. in a water bath, and mixed/vortexed until all components are completely dissolved and form a clear solution. Approximately 1 mL of the hot solution was filled into a 5 mL prefilled syringe, and steam-sterilized under 121° C. for 20 minutes. They appeared as a homogeneous opaque gel with or without steam sterilization after cooling down to room temperature at 10 to 20 wt % gelling agent level and are injectable with 21 G needle at 10 and 15 wt % level. At 20% level, it takes 1:25 minutes to start gelation, and 5 minutes to complete gelation. The formulation became a relatively hard gel and is difficult to be injected with a 21 G needle.

TABLE 6

CO and HCO ratio

| Sample ID | CO (g) | HCO (g) | BUP (mg) |
|---|---|---|---|
| HCO F01 | 1.64 | 0.20 | 160 |
| HCO F02 | 1.54 | 0.30 | 160 |
| HCO F03 | 1.44 | 0.40 | 160 |

Solid partial glycerides of fatty acids include G43/01, a mixture of $C_8$ to $C_{18}$ triglycerides with a melting point of 42° C. to 45° C.; GELEOL™, a glyceryl monostearate with a melting point of 54° C. to 64° C.; COM, a glyceryl behenate with a melting point of 65° C. to 77° C.; and G39/01, a glyceride mixture of mono-, di-, and triglycerides of $C_{12}$ to $C_{18}$ fatty acids with a melting point of 37° C. to 40° C. These were tested as gelling agents to enable castor oil to form semi-solid gel formulations in the presence of local anesthetic.

Example 5. G43/01

The G43/01 mixture of $C_8$ to $C_{18}$ triglycerides has a melting point of 42 to 45° C. The CO and G43/01 ratio study is shown in Table 7. The targeted amount of each component was weighed to a glass vial and heated to about 75° C. in a water bath, and mixed/vortexed until all components are completely dissolved and form a clear solution.

It takes about 8:30 minutes and 6:30 minutes to start gelation, and 15:00 minutes and 13:00 minutes to complete gelation for 15% and 20% G43/01 respectively.

Approximately 1 mL of the hot solution was filled into a 5 mL prefilled syringe, and steam-sterilized under 121° C. for 20 minutes. They appeared as a homogeneous opaque gel with or without steam sterilization after cooling down to room temperature at 10 to 20 wt % gelling agent level, and are injectable with 21 G needle.

TABLE 7

CO and G43/01 ratio study

| Sample ID | CO (g) | G43/01 (g) | BUP (mg) |
|---|---|---|---|
| G43/01 F01 | 1.64 | 0.20 | 160 |
| G43/01 F02 | 1.54 | 0.30 | 160 |
| G43/01 F03 | 1.44 | 0.40 | 160 |

Example 6. COM

The CO and COM ratio study is shown in Table 8. This solid glyceryl behenate has a melting point of 65 to 77° C. The targeted amount of each component was weighed to a glass vial and heated to about 80° C. in a water bath, and mixed/vortexed until all components are completely dissolved and form a clear solution.

Approximately 1 mL of the hot solution filled into a 5 mL prefilled syringe, and steam-sterilized under 121° C. for 20 minutes. It appeared as a homogeneous opaque gel with or without steam sterilization after cooling down to room temperature at 10 to 20 wt % gelling agent level. It is injectable with 21 G needle at 10 and 15 wt % level. At 20% level, the formulation became a relatively hard gel and is not injectable with a 21 G needle.

TABLE 8

CO and COM ratio study

| Sample ID | CO (g) | COM (g) | Bup Amount (mg) |
|---|---|---|---|
| Com F01 | 1.64 | 0.20 | 160 |
| Com F02 | 1.54 | 0.30 | 160 |
| Com F03 | 1.44 | 0.40 | 160 |

Example 7. GEL

The CO and GEL ratio study is shown in Table 9. This solid glyceryl monostearate has a melting point of 54 to 64° C. The targeted amount of each component was weighed to a glass vial and heated to about 75° C. in a water bath, and mixed/vortexed until all components are completely dissolved and form a clear solution.

Approximately 1 mL of the hot solution was filled into a 5 mL prefilled syringe, and steam-sterilized under 121° C. for 20 minutes. They appeared as a homogeneous opaque gel with or without steam sterilization after cooling down to room temperature at 10 to 20 wt % gelling agent level, and are injectable with 21 G needle.

TABLE 9

CO and GEL ratio study

| Sample ID | CO (g) | GEL (g) | BUP (mg) |
|---|---|---|---|
| Gel F01 | 1.64 | 0.20 | 160 |
| Gel F02 | 1.54 | 0.30 | 160 |
| Gel F03 | 1.44 | 0.40 | 160 |

Example 8. WIT E85 and WIT E76

Mixtures of triglyceride, diglyceride or monoglyceride such as WIT E85 with a melting point of 42° C. to 44° C., and WIT E76 with a melting point of 37° C. to 39° C., were tested as gelling agents to enable castor oil to form semi-solid gel formulations in the presence of local anesthetic.

The CO and WIT E85 ratio study is shown in Table 10. The targeted amount of each component was weighed to a glass vial and heated to about 75° C. in a water bath, and mixed/vortexed until all components are completely dissolved and form a clear solution.

It takes about 8:30 minutes and 6:30 minutes to start gelation, and about 15:00 minutes and 13:30 minutes to complete gelation.

Approximately 1 mL of the hot solution was filled into a 5 mL prefilled syringe, and steam-sterilized under 121° C. for 20 minutes. They appeared as a homogeneous opaque gel with or without steam sterilization after cooling down to room temperature at 10 to 20 wt % gelling agent level, and are injectable with 21 G needle.

TABLE 10

CO and WIT E85 ratio study

| Sample ID | CO (g) | WIT E85 (g) | BUP (mg) |
|---|---|---|---|
| Wit F01 | 1.64 | 0.20 | 160 |
| Wit F02 | 1.54 | 0.30 | 160 |
| Wit F03 | 1.44 | 0.40 | 160 |

Example 9. Natural Sterol Esters, Lanolin (LAN)

LAN is an "ester", structurally similar to "glyceryl ester", and is compatible with triglyceride castor oil. It has a melting point of 38°. At 18 wt % LAN, it takes about 3:30 minutes to start gelation, but 7:00 minutes to complete gelation due to its high viscosity.

The CO and LAN ratio study is shown in Table 11. The targeted amount of each component was weighed to a glass vial and heated to about 75° C. in a water bath, and mixed/vortexed until all components are completely dissolved and form a clear solution.

Approximately 1 mL of the hot solution was filled into a 5 mL prefilled syringe, and steam-sterilized under 121° C. for 20 minutes. They appeared as a homogeneous opaque gel with or without steam sterilization after cooling down to room temperature at 10 to 20 wt % gelling agent level, and are injectable with 21 G needle.

TABLE 11

CO and LAN ratio study

| Sample ID | CO (g) | LAN (g) | BUP (mg) |
|---|---|---|---|
| Lan F01 | 1.64 | 0.20 | 160 |
| Lan F02 | 1.54 | 0.30 | 160 |
| Lan F03 | 1.44 | 0.40 | 160 |

Example 10. Loteprednol Etabonate

Loteprednol (ALREX® or LOTEMAX®) in the form of the ester loteprednol etabonate is a corticosteroid used in ophthalmology. Ocular applications for this drug include the treatment of inflammation of the eye due to allergies (according to the prescription information sheet), as well as chronic forms of keratitis (e.g., adenoviral or Thygeson's keratitis), vernal keratoconjunctivitis, pingueculitis, and episcleritis. The drug has little or no effect on intraocular pressure.

The semi-solid formulation, Gel 001 LOTE: CO/SUP DM/LOTE (77.8/19.5/2.7), was prepared by weighing castor oil, SUP DM and the drug into a glass vial, and closing the lid. The vehicle components were melted by heating to 90° C. in a water bath, and loteprednol was dissolved to form a clear solution and became a semi-transparent soft paste after cooling down to room temperature.

FIG. 1 shows loteprednol etabonate release from castor oil gel formulation gelled by SUP DM, yielding loteprednol release profile for 7 days since loteprednol etabonate is relatively water soluble.

Example 11. Latanoprost

Latanoprost is used for treating glaucoma or ocular hypertension by reducing intraocular pressure.

The semi-solid formulations, Gel 001 LATA: CO/SUP CM/LATA (73.8/21.4/4.8), Gel 002 LATA: CO/SUP DM/LATA (80/15/5), were prepared by weighing castor oil, SUP CM or SUP DM and the drug into a glass vial, and closing the lid. The vehicle components were melted by heating to 75° C. in a water bath, and latanoprost was dissolved to form a clear solution and became a semi-transparent soft gel after cooling down to room temperature.

Figure 2:
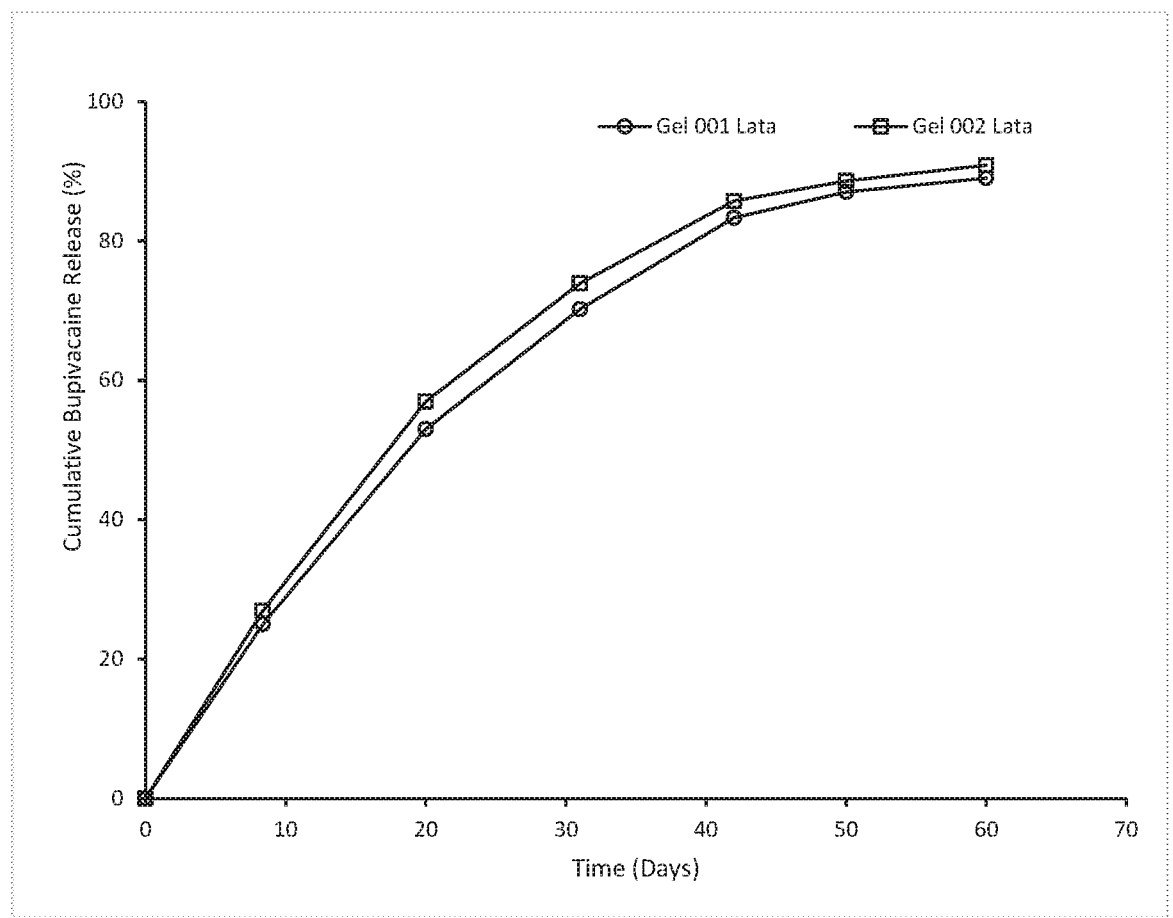
FIG. 2 shows release of latanoprost (LATA) from a formulation comprising castor oil gel gelled by SUP DM or SUP CM. Gel 001 LATA: CO/SUP CM/LATA (73.8/21.4/4.8), Gel 002 LATA: CO/SUP DM/LATA (80/15/5) in PBS, pH 7.4, 37° C.

FIG. 2 shows latanoprost release from castor oil gel formulation gelled by SUP DM and SUP CM. Latanoprost is a relatively hydrophobic drug and was released in a sustained manner for 2 months for the two gel formulations with two gelling agents.

Example 12. Celecoxib

Celecoxib is marketed under the trade names CELEBREX®, ONSENAL®, ARTICOX®, ARTICOXIB®, ARTIFLEX®, ARTILOG®, ARTIX®, ARTRIXIB®, BLOCKTEN®, CADITAR®, CEFINIX®, CELACT®, CELEBRA®, and VALDYNE®. Celecoxib, a selective cyclooxygenase-2 (COX-2) inhibitor, is a nonsteroidal anti-inflammatory drug (NSAID) used to manage symptoms of various types of arthritis pain including osteoarthritis and in familial adenomatous polyposis (FAP) to reduce precancerous polyps in the colon.

The semi-solid formulations, Gel 001 CEL: CO/SUP CM/CEL (73.8/21.4/4.8), Gel 002 CEL: CO/SUP DM/CEL (80.9/14.3/4.8), were prepared by weighing castor oil, SUP CM or SUP DM and the drug into a glass vial, and closing the lid. The vehicle components were melted by heating to 75° C. in a water bath, and celecoxib was partially dissolved (approximately 1 wt % was dissolved in the vehicle) to form a clear solution with micronized celecoxib drug particles suspended. A nice homogeneous soft semi-solid gel suspension formulation was formed after cooling down to room temperature.

Figure 3:
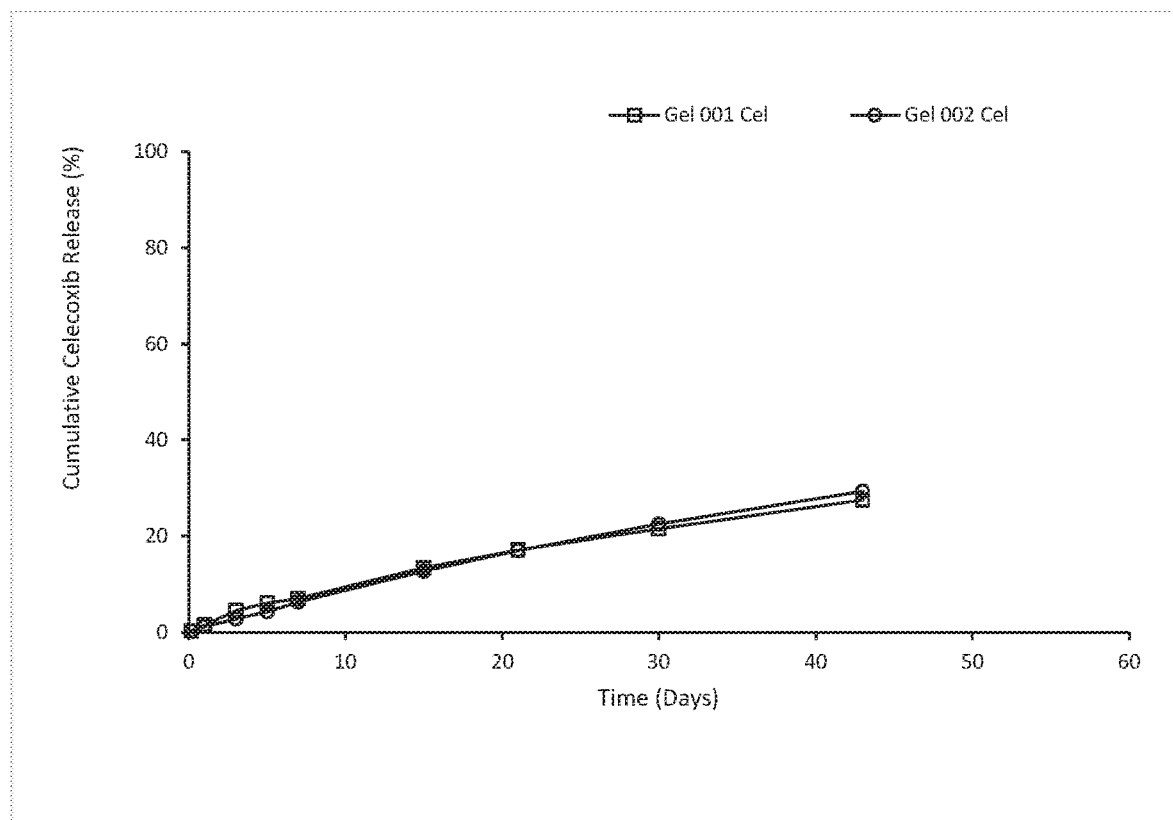
FIG. 3 shows release of celecoxib (CEL) from a formulation comprising castor oil gelled by SUP DM or SUP CM. Gel 001 CEL: CO/SUP CM/CEL (73.8/21.4/4.8), CO/SUP DM/CEL (80.9/14.3/4.8) in PBS, pH 7.4, 37° C.

FIG. 3 shows celecoxib release from castor oil gel formulation gelled by SUP DM and SUP CM. Celecoxib is a very hydrophobic drug and yielded similar celecoxib release of about 27.5% and 29.3%, respectively, for the two suspension gel formulations at Day 43. Celecoxib is released in a sustained manner for more than 3 months.

Example 13. Triamcinolone Acetonide

Triamcinolone as an acetonide salt is marketed as ARISTOCORT®, AZMACORT®, KENACORT®, KENA- LOG®, NINCORT®, RATIO-TRIACOMB®, TRIADERM,® TRIANEX®, TRICORT®, TRICORTONE®, TRILONE®, TRISTOJECT®, and VOLON A®. Routes of administration include oral, topical, intramuscular, intra-articular, and intrasynovial. Triamcinolone is a corticosteroid used to treat various inflammatory conditions in the body from allergic rhinitis to acute exacerbations of multiple sclerosis. Triamcinolone is also used as an adjunct treatment of osteoarthritic knee pain.

The semi-solid formulations, Gel 001 TA: CO/SUP CM/TA (73.8/21.4/4.8), Gel 002 TA: CO/SUP DM/TA (80.9/14.3/4.8), were prepared by weighing castor oil, SUP CM or SUP DM and the drug into a glass vial, and closing the lid. The vehicle components were melted by heating to 75° C. in a water bath, and celecoxib was partially dissolved (less than 1 wt % was dissolved in the vehicle) to form a clear solution with micronized triamcinolone acetonide drug particles suspended. A nice homogeneous soft semi-solid gel suspension formulation was formed after cooling down to room temperature.

Figure 4:
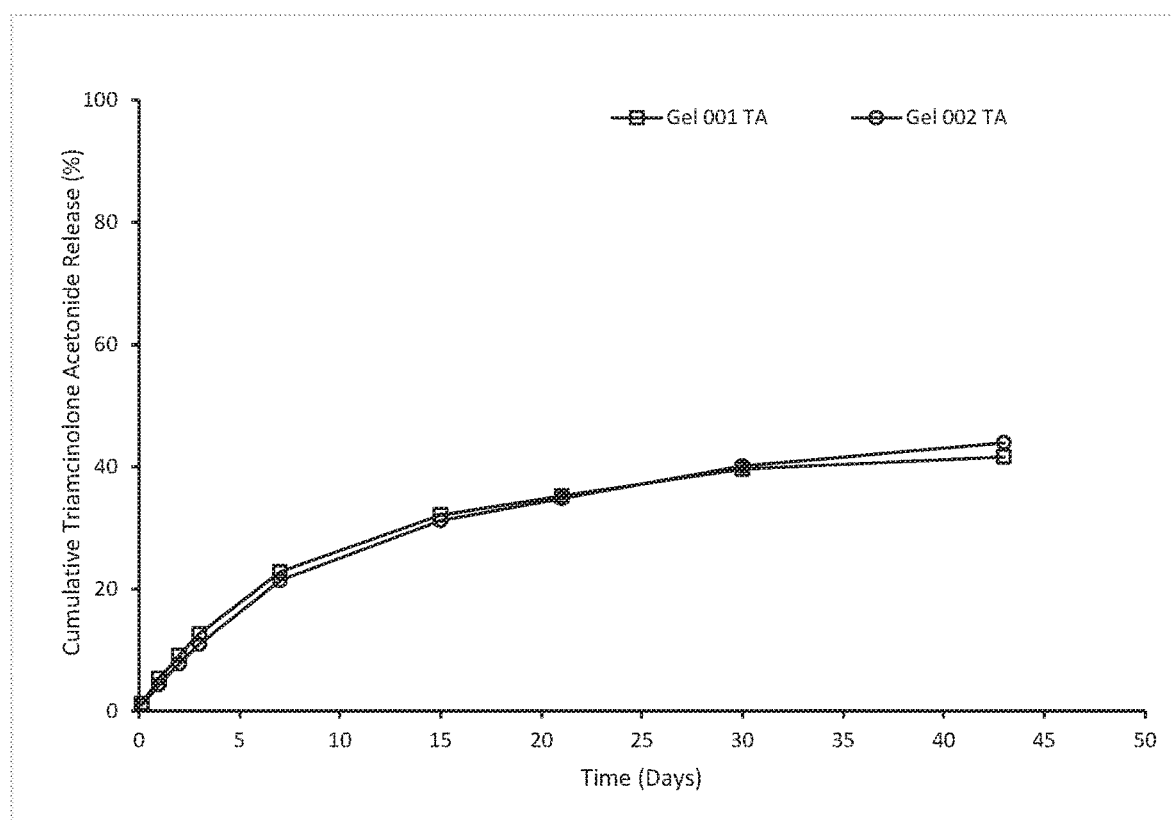
FIG. 4 shows release of triamcinolone acetonide (TA) from a formulation comprising castor oil gelled by SUP DM or SUP CM. Gel 001 TA: CO/SUP CM/TA (73.8/21.4/4.8), Gel 002 TA: CO/SUP DM/TA (80.9/14.3/4.8) in PBS, pH 7.4, 37° C.

FIG. 4 shows triamcinolone acetonide release from castor oil gel formulation gelled by SUP DM and SUP CM, yielding similar triamcinolone release of about 41.6% and 43.9% respectively for the triamcinolone suspension gel formulations with the two gelling agents at Day 43. Triamcinolone is released in a sustained manner for more than 2 months.

Example 14. Betamethasone Valerate

Betamethasone valerate salt is marketed as BETAMETHACOT®, BETA-VAL®, LUXIQ®, QUALISONE®, VALISONE®, BETACORT®, BETNOVATE®, BETNOVATE®, CELESTODERM®, CELESTODERM®, and ECTOSONE®. It is a glucocorticoid given orally, parenterally, by local injection, by inhalation, or applied topically in the management of various disorders in which corticosteroids are indicated including osteoarthritic knee pain.

The semi-solid formulations, Gel 001 BETV: CO/SUP CM/BETV (75.9/22.1/2.0), Gel 002 BETV: CO/SUP DM/BETV (83.3/14.7/2.0), were prepared by weighing castor oil, SUP CM or SUP DM and the drug into a glass vial, and closing the lid. The vehicle components were melted by heating to 75° C. in a water bath, and latanoprost was dissolved to form a clear solution and became a semi-transparent soft gel after cooling down to room temperature.

Figure 5:
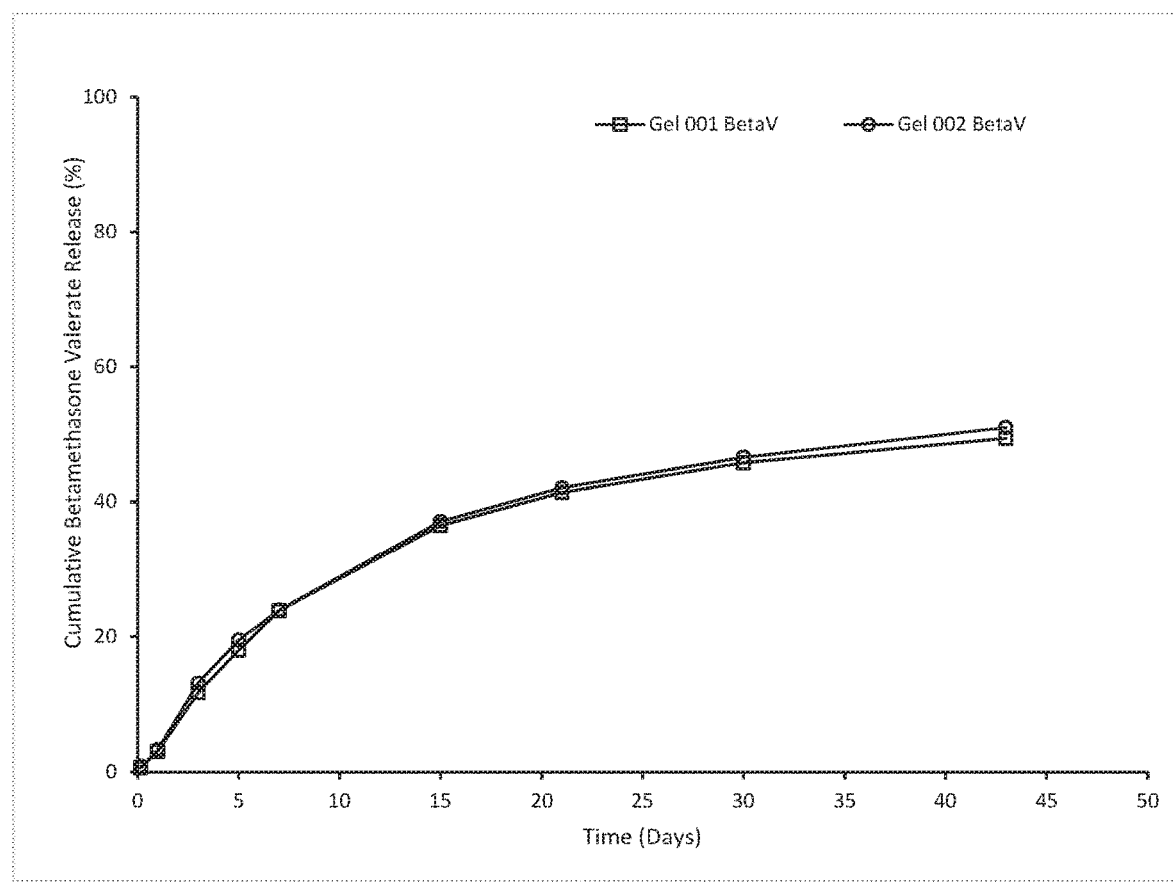
FIG. 5 shows release of betamethasone valerate (BETV) from a formulation comprising castor oil gelled by SUP DM or SUP CM. Gel 001 BETV: CO/SUP CM/BETV (75.9/22.1/2.0), Gel 002 BETV: CO/SUP DM/BETV (83.3/14.7/2.0) in PBS, pH 7.4, 37° C.

FIG. 5 shows betamethasone valerate release from castor oil gel formulation gelled by SUP DM and SUP CM. Betamethasone valerate is a relatively hydrophobic drug and yielded similar betamethasone release of about 50% at Day 43 for the two gel formulations with two gelling agents. Betamethasone is released in a sustained manner for more than 2 months.

Example 15. In Vitro Release

The semi-solid local anesthetic semi-solid pharmaceutical compositions below were prepared as follows: The local anesthetics, castor oil, and gelling agents, were added to a glass container, and then heated to about 70° C. to 90° C. to completely melt the gelling agents into a solution, and completely dissolve the active drugs into the delivery vehicle to from a clear solution while mixing. After achieving a homogeneous and uniform pharmaceutical composition, the local anesthetic semi-solid formulation was then cooled down to ambient temperature naturally. The semi-solid formulations described herein appeared as a semi-transparent or opaque soft gel.

Gel 001 LOTE: CO/SUP DM/LOTE (77.8/19.5/2.7)
Gel 001 LATA: CO/SUP CM/LATA (73.8/21.4/4.8)
Gel 002 LATA: CO/SUP DM/LATA (80/15/5)
Gel 001 CEL: CO/SUP CM/CEL (73.8/21.4/4.8)
Gel 002 CEL: CO/SUP DM/CEL (80.9/14.3/4.8)
Gel 001 TA: CO/SUP CM/TA (73.8/21.4/4.8)
Gel 002 TA: CO/SUP DM/TA (80.9/14.3/4.8)
Gel 001 BETV: CO/SUP CM/BETV (75.9/22.1/2.0)
Gel 002 BETV: CO/SUP DM/BETV (83.3/14.7/2.0)

The in vitro release profiles of local anesthetic were evaluated by placing approximately 50 mg of the formulation enclosed in porous membrane into a glass bottle with 100 mL of PBS at pH 7.4 without stirring. At various time points, samples were taken and analyzed for local anesthetic content by UV-Vis at 220 nm, for loteprednol by UV-Vis at 277 nm, and for latanoprost by UV-Vis at 210 nm. The content of celecoxib, triamcinolone acetonide, and betamethasone valerate was analyzed high-performance liquid chromatography (HPLC). Chromatographic conditions were as follows: (1) Column: Welch Xtimate C18, 5 μm, 4.6×250 mm; (2) Mobile phase: 20 mM ammonium acetate (pH 8.0): acetonitrile (38:62); (3) Wavelength of detection: 210 nm for celecoxib at retention time (RT) 9.9 min; 240 nm for triamcinolone acetonide at RT 4.0 min; 270 nm for betamethasone valerate at RT 10.5 min; (4) Column temperature: 21° C.; (6) Injection volume: 100 μl; (6) Flow rate: 1.0 ml/min; (7) Run time: 15 minutes.

Mechanism for Controlled Release of the Formulations Described Herein

When the semi-solid gel formulation is placed into an aqueous environment, water will diffuse into the semi-solid lipid matrix, the active agent on the formulation surface will first gradually dissolve into the surrounding aqueous media. As aqueous media penetrates into the semi-solid lipid gel, the semi-solid lipid erodes, both by surface and bulk erosion, and gradually dissolve into the surrounding aqueous media, the active agent will gradually diffuse out and released into the surrounding aqueous media in a sustained manner over a period of time.

Factors that Affect the Drug Release Rate

The release rate of active agent is affected both by the semi-solid gel vehicle components and the active ingredient and can be regulated in a variety ways to accommodate the desired duration of therapeutic effect.

For the semi-solid gel vehicles, the release rate of active agent can be increased or decreased by using different types/levels/amounts/ratios hydrophobic glyceride gelling agents with different water solubility and/or dissolution rates. As water solubility and dissolution rate of the semi-solid lipids decrease, it will take longer for the semi-solid gel to be dissolved and absorbed, thus resulting longer duration of drug release as long as the active agent exhibits sufficient low solubility.

In addition, lower water solubility forms of active ingredient such as their base forms, or as complexes with fatty acids may be used to delay the release of active ingredient.

Example 16. Viscosity Determination

This purpose of the viscosity measurement for the semi-solid formulations is to demonstrate that the semi-solid formulations disclosed are readily injectable through a 23 G to 21 G needle.

Viscosity Determination Procedure:

The viscosity of the semi-solid formulations was determined on a calibrated Brookfield RVDV-I Prime CP model viscometer using cone spindle CPE-51. The semi-solid formulation samples stored in sealed glass vials were first heated to about 40° C. to 50° C. in an oven until the samples became a flowable viscous liquid. Then approximately 0.5 gram of each sample was weighed into the center the warmed sample cup. Avoid bubbles when possible. Attach the sample cup to the viscometer and measure the viscosity at an appropriate speed of rotation so that the percentage torque is between 10% and 100%. Record the viscosity and percentage torque at the target temperature. Due to the soft paste nature of these materials at room temperature, the viscosity of semi-solid formulations was determined at 30° C. at that point the semi-solid formulations become a flowable viscous liquid/semi-solid under pressure. Centipoise (cP) and milliPascal seconds (mPa·s) are the CGS and SI units for viscosity. 1 cP=1 mPa·s. The viscosity of all the semi-solid formulations was measured at 30° C.

Viscosity Data

Superior Physiochemical Profile—Low-Viscosity Gel Formulations

Castor oil is a liquid with a viscosity of approximately 700 cP at 25° C. and 451 cP at 30° C.

The viscosity value of castor oil gel formulations comprising active ingredient with active ingredient exhibited low viscosity characteristics, ranging from 285 cPs to 347 cPs at 30° C. The gelling agents served to gel castor oil and to reduce the viscosity of the formulation to improve its syringeability and injectability.

Even these formulations are in the form of gel, they are readily injected through a 21 G needle allowing for a single easy administration for local treatment.

Viscosity Values of Castor Oil Gel Formulation

The viscosity results for the castor oil gel formulations with different active ingredients were summarized in Table 12. The viscosity of all the semi-solid formulations was measured at 30° C.

TABLE 12

Viscosity results for castor oil gel formulations with different active ingredients

| Gel formulation composition (wt %) | Viscosity (cP) at 30° C. |
|---|---|
| CO/SUP DM/LOTE (77.8/19.5/2.7) | 305 |
| CO/SUP CM/LATA (73.8/21.4/4.8) | 290 |
| CO/SUP DM/LATA (80/15/5) | 340 |
| CO/SUP CM/CEL (73.8/21.4/4.8) | 288 |
| CO/SUP DM/CEL (80.9/14.3/4.8) | 347 |
| CO/SUP CM/TA (73.8/21.4/4.8) | 291 |
| CO/SUP DM/TA (80.9/14.3/4.8) | 345 |
| CO/SUP CM/BETV (75.9/22.1/2.0) | 285 |
| CO/SUP DM/BETV (83.3/14.7/2.0) | 343 |

The viscosity value of castor oil gel formulations with different active ingredients exhibited low viscosity characteristics, ranging from 285 cPs to 347 cPs at 30° C. All the gelling agents are waxy solids and acts as lubricant due to the waxy property from the long alkyl chains of fatty acids to reduce the viscosity of gel formulations. The active ingredient can also act as a plasticizer and reduce the viscosity of the gel formulations.

All the castor oil gel formulations with and without anti-inflammatory listed in Table 12 are readily injectable with mechanical pressure (shear force) with a 21 G needle.

Example 17. Evaluation of Skin Reactions

The following bupivacaine castor oil gel formulations with and without anti-inflammatory along with previously developed semi-solid formulations using 5701 were administered to each animal by subcutaneous injection at the cleanly shaved dorsal aspect of the thorax.

Semi-solid 5701: S701/SUP A/BUP (79/13/8)

Semi-solid S701+BetV: S701/SUP A/BUP (78.95/13/8/0.05)

Gel DM: CO/SUP DM/BUP (81/11/8)

Gel DM+BetV: CO/SUP DM/BUP/BETV (80.95/11/8/0.05)

Injection site reaction of edema/erythema data were evaluated according Table 13.

TABLE 13

Evaluation of Skin Reactions

| | Score |
|---|---|
| Erythema and Eschar Formation | |
| No erythema | 0 |
| Very slight erythema (barely perceptible) | 1 |
| Well-defined erythema | 2 |
| Moderate to severe erythema | 3 |
| Severe erythema (beet redness) to slight eschar formation (injuries in depth) | 4 |
| Edema Formation | |
| No edema | 0 |
| Very slight edema (barely perceptible) | 1 |
| Slight edema (edges of area well-defined by definite raising) | 2 |
| Moderate edema (raised approximately 1 mm) | 3 |
| Severe edema (raised more than 1 mm and extending beyond area of exposure) | 4 |

Injection site edema/erythema results for the tested formulations is shown in Tables 14 and 15. Palpable masses (edema score of 2 to 3), attributed to depositing of the semi-solid formulations, were evident at the dosing area in all animals right after injection. Semi-solid S701 exhibited edema at Day 1 and Day 2, and gradually subsided from Day 3 to Day 8. In the presence of 0.05% betamethasone valerate, edema was eliminated. Semi-solid S701 also exhibited moderate erythema at Day 1 and Day 2, and gradually subsided from Day 3 to Day 8. In the presence of 0.05% betamethasone valerate, erythema was reduced at Day 1 and Day 2.

The castor oil gel/DM formulation, Gel DM, only exhibited very slight or minimal edema and erythema at the injection sites. This effect was lower in the presence of betamethasone valerate.

TABLE 14

Skin reaction (Edema) results after 0.5 mL subcutaneous injection

| Semi-solid gel Formulation ID | Day 1 | Day 2 | Day 3 | Day 4 | Day 5 | Day 6 | Day 7 | Day 8 |
|---|---|---|---|---|---|---|---|---|
| S701 | 4.0 | 4.0 | 3.3 | 2.3 | 2.0 | 2.0 | 1.3 | 1.3 |
| S701 + BETV | 2.0 | 1.7 | 1.7 | 1.0 | 1.0 | 1.0 | 1.0 | 0.7 |
| Gel DM | 3.0 | 2.5 | 2.5 | 2.5 | 2.0 | 2.0 | 1.5 | 1.5 |
| CO DM + BETV | 2.5 | 2.0 | 2.0 | 1.5 | 1.5 | 1.5 | 1.0 | 1.0 |

TABLE 15

Skin reaction (Erythema) results after
0.5 mL subcutaneous injection

| Semi-solid Formulation ID | Day 1 | Day 2 | Day 3 | Day 4 | Day 5 | Day 6 | Day 7 | Day 8 |
|---|---|---|---|---|---|---|---|---|
| S701 | 3.0 | 3.0 | 2.0 | 1.7 | 1.7 | 1.0 | 0.7 | 0.7 |
| S701 + BETV | 1.7 | 1.3 | 1.0 | 1.0 | 0.7 | 0.3 | 0.3 | 0.3 |

Example 18. In Vivo Rat Sciatic Nerve Blockade Tests

Male rats weighing between 200 g and 250 g were used to assess the duration of nerve conduction block, which induced by each of the different semi-solid formulations had been tested. The rats were handled daily and habituated to the testing paradigm for at least 60 minute prior to examination. Sensory and motor blockade were examined as described below. In addition to sensory testing, motor testing was performed at each time point to examine the ability of the rats to move their hind leg by gait posture and paw placing. Animals were handled and cared in compliance with institutional, state, and federal animal welfare regulation. The protocol was approved by IACAC.

All rats were anesthetized with 3.5% to 4.0% isoflurane in oxygen and maintained with 1.5%-2.0% isoflurane. Under aseptic condition, the left thigh area was shaved and an incision was made on the upper ⅓ portion. The thigh muscles were gently dissected by blunt dissection to expose the sciatic nerve. Semi-solid gel formulations were placed adjacent to the sciatic nerve under direct vision in the fascia plane deep to the hamstrings and the site. The most superficial fascia layer was closed with a single suture. The edges of the outer skin were approximated and closed with surgical staples. For all rats, drug-containing semi-solid formulations were implanted on the left side of sciatic nerve.

Hot-plate measurement: for each time-point, the rat was put on 56° C. hot-plate and the latency of lifting the hind paw was recorded (for both paws of the animal) for three times with intervals at least 5 minutes. A cutoff latency of 10 seconds was used to prevent development of hyperalgesia or injury. The average of three readings was used as the final reading for the particular time-point.

Paw placing: for both paws, the animals were held gently by a trained researcher and the dorsal paw, one at a time, was slowly slid over a edge of test platform until the toes were reached and repeated 5 times. At each time, if the rat successfully places its testing paw onto the surface of the platform, it was scored as 1 (therefore, the maximum score is 5 for each paw) and as 0 if it fails.

Paw motor ability measurement: The paw motor ability test, utilizing a scale of 1 to 4, evaluates the animal's ability to hop and place weight on its hind leg, according to following levels (Castillo, 1996, Anesthesiology 85:1157-66):

(1) normal appearance.
(2) intact dorsiflexion, but impaired splaying toes when elevating the tail of rat.
(3) completely plantar flexion without splaying ability.
(4) number 3 plus impaired gait.

The paw motor ability assessment was used for each time-point as well. For both paws, the animals were held gently by a trained researcher dorsally.

Two weeks following the administration of bupivacaine the surgical site skin was examined to observe if any affection on wound healing. Further, sites where the semi-solid formulation was administered were re-opened and examined visually by naked eyes under anesthesia.

1. Bupivacaine Castor Oil Gel Formulation

The pharmacodynamic activity of bupivacaine released from castor oil gel formulation yielded greater analgesic activity compared to bupivacaine in castor oil alone when evaluated in the rat sciatic nerve blockade model. A bupivacaine castor oil solution formulation containing 8 wt % bupivacaine was used as a control formulation. Castor oil bupivacaine oil solution yielded a limited analgesic response of approximately 4-6 hours in the rat sciatic nerve blockade model, thanks to its relatively high viscosity and relatively slow dissolution of bupivacaine free base into body fluid.

Bupivacaine in formulations of castor oil in combination with gelling agents provides robust sensory and motor blockade over the first 24 hours, and extended partial blockade up to 72 hours commensurate with the degree of analgesia (moderate block for the second day, partial block for the third day, which underscores the pain intensity profile of typical surgical patients with extreme pain for the first day, moderate pain for the second day, and only minor pain for the third day.)

The bupivacaine castor oil solution formulation only yielded dense motor blockade for two hours and extended partial blockade up to six hours. Motor function was reversible in all groups, which had returned to normal values 72 hours post administration.

Stability of CO Semi-Solid Gel Formulations

These CO gel formulations of five active ingredients, loteprednol, latanoprost, celecoxib, triamcinolone, and betamethasone are stable under room temperature without phase separation or precipitation during storage for one month.

What is claimed:

1. A pharmaceutical formulation, comprising:
   (A) a glyceride mixture comprising:
      (i) triglyceride of ricinoleic acid; and
      (ii) a gelling agent selected from the group consisting of (a) a mixture of $C_{12}$ to $C_{18}$ triglycerides, (b) a mixture of $C_8$ to $C_{18}$ triglycerides, (c) a mixture of hydrogenated coco-glycerides, (d) a mixture of $C_{10}$ to $C_{18}$ triglycerides, and other solid glycerides with a melting point between 37° C. and 75° C.,
      wherein a ratio of the triglyceride of ricinoleic acid to the gelling agent is from 50:1 to 2:1 (w:w); and
   (B) an active ingredient selected from the group consisting of loteprednol, latanoprost, celecoxib, triamcinolone, and betamethasone, or a pharmaceutically acceptable salt thereof, and optionally, a second corticosteroid, an analgesic or an anti-inflammatory compound,
   wherein a total concentration of the active ingredient is 0.01-60 wt % in the glyceride mixture,
   wherein the pharmaceutical formulation is a semi-solid gel which is biocompatible, bioerodible, and homogeneous,
   wherein the semi-solid gel has a viscosity of 50-700 cPs at 30° C., and
   wherein less than 80% of the active ingredient is released from a depot of the semi-solid gel in one week when measured in vitro at 37° C.

2. The pharmaceutical formulation of claim 1, wherein the glyceride mixture comprises a mixture of $C_{12}$ to $C_{18}$ triglycerides.

3. The pharmaceutical formulation of claim 1, wherein the ratio of the triglyceride of ricinoleic acid to the gelling agent is from 8:1 to 2.5:1 (w:w).

4. The pharmaceutical formulation of claim 1, wherein less than 60% of the active ingredient is released from the depot of the semi-solid gel in one week when measured in vitro at 37° C.

5. The pharmaceutical formulation of claim 1, wherein the pharmaceutical formulation releases the active ingredient for at least two weeks when measured in vitro at 37° C.

6. The pharmaceutical formulation of claim 1, wherein a viscosity of the glyceride mixture at 37° C. is 200 to 400 cPs at 30° C.

7. The pharmaceutical formulation of claim 1, wherein the glyceride mixture has an aqueous solubility of less than 1 mg/ml in a buffer of physiological pH at 37° C.

8. The pharmaceutical formulation of claim 1, wherein the triglyceride of ricinoleic acid is castor oil.

9. The pharmaceutical formulation of claim 1, wherein the triglyceride of ricinoleic acid is castor oil, the gelling agent is SUP DM or SUP CM, and the glyceride mixture comprises castor oil:(SUP DM or SUP CM) at a relative concentration of 6:1 to 3:1 (w:w).

10. The pharmaceutical formulation of claim 9, wherein less than 80% of the active ingredient is released from the depot of the semi-solid gel in one week when measured in vitro at 37° C.

11. The pharmaceutical formulation of claim 1, comprising a therapeutically effective amount of at least one active ingredient selected from the group consisting of celecoxib, triamcinolone, and betamethasone for treating pain and inflammation.

12. The pharmaceutical formulation of claim 1, comprising a therapeutically effective amount of loteprednol or latanoprost for treating ophthalmic disease.

13. The pharmaceutical formulation of claim 1, further comprising at least one active ingredient selected from the group consisting of the second glucocorticoid, the analgesic or the anti-inflammatory agent.

14. The pharmaceutical formulation of claim 1, wherein the formulation is without a preservative.

15. A pharmaceutical formulation, consisting of comprising castor oil, a mixture of $C_{12}$ to $C_{18}$ triglycerides, and a therapeutically effective amount of an active ingredient selected from the group consisting of loteprednol, latanoprost, celecoxib, triamcinolone, and betamethasone, wherein the pharmaceutical formulation is a semi-solid gel which is biocompatible, bioerodible, and homogeneous, wherein the semi-solid gel has a viscosity of 50-700 cPs at 30° C., and wherein less than 80% of the active ingredient is released from a depot of the semi-solid gel in one week when measured in vitro at 37° C.

16. The pharmaceutical formulation of claim 15, wherein the mixture of $C_{12}$ to $C_{18}$ triglycerides comprises a ratio of the castor oil and the gelling agent at a relative concentration of 6:1 to 3:1 (w:w).

17. The pharmaceutical formulation of claim 15, wherein the viscosity of the pharmaceutical formulation is from 285 cPs to 347 cPs at 30° C.

18. The pharmaceutical formulation of claim 15, wherein less than 80% of the active ingredient is released from the depot of the semi-solid gel in one month when measured in vitro at 37° C.

19. The pharmaceutical formulation of claim 1, wherein the mixture of $C_{12}$ to $C_{18}$ triglycerides is SUP DM or SUP CM, the mixture of $C_8$ to $C_{18}$ triglycerides is G43/01, the mixture of hydrogenated coco-glycerides is WIT E85 or WIT E76, and the mixture of $C_{10}$ to $C_{18}$ triglycerides is SUP D.

20. The pharmaceutical formulation of claim 15, wherein the mixture of $C_{12}$ to $C_{18}$ triglycerides is SUP DM or SUP CM.

* * * * *